United States Patent [19]

Columbus

[11] 4,233,029
[45] Nov. 11, 1980

[54] LIQUID TRANSPORT DEVICE AND METHOD

[75] Inventor: Richard L. Columbus, Rochester, N.Y.

[73] Assignee: Eastman Kodak Company, Rochester, N.Y.

[21] Appl. No.: 954,689

[22] Filed: Oct. 25, 1978

[51] Int. Cl.² .............................................. G01N 31/00
[52] U.S. Cl. ............................ 23/230 R; 204/195 R; 204/195 M; 422/55; 422/58; 422/68; 422/100
[58] Field of Search ................... 356/244; 23/230 R; 422/55, 56, 57, 58, 68, 100; 204/195 R, 195 M

[56] References Cited

U.S. PATENT DOCUMENTS

| | | | |
|---|---|---|---|
| 3,198,064 | 8/1965 | Moore | 356/244 |
| 3,415,502 | 12/1968 | Munters | 261/DIG. 11 |
| 3,450,393 | 6/1969 | Munters | 261/112 |
| 3,619,072 | 11/1971 | O'Hara | 356/246 |
| 3,690,836 | 9/1972 | Buissiere et al. | 422/56 |
| 3,715,192 | 2/1973 | Wenz et al. | 422/56 |
| 3,961,346 | 6/1976 | White | 356/244 |
| 3,992,158 | 11/1976 | Przyblowicz et al. | 422/57 |
| 4,002,056 | 1/1977 | Kopito et al. | 73/53 |
| 4,022,521 | 5/1977 | Hall et al. | 356/244 X |
| 4,053,381 | 10/1977 | Hamblen et al. | 204/195 R X |

*Primary Examiner*—Arnold Turk
*Attorney, Agent, or Firm*—Dana M. Schmidt

[57] ABSTRACT

A liquid transport device and method are disclosed, for controlled liquid flow. The device contains opposed surfaces providing a controlled capillary flow zone, each surface including means for directing flow along predetermined paths and at least one surface including means to permit liquid introduction between the surfaces. At least a portion of the paths of one surface form a positive angle with respect to the paths of the directly opposing portion of the other surface, whereby controlled multidirectional flow of liquid introduced between the surfaces occurs with a predetermined peripheral configuration.

33 Claims, 14 Drawing Figures

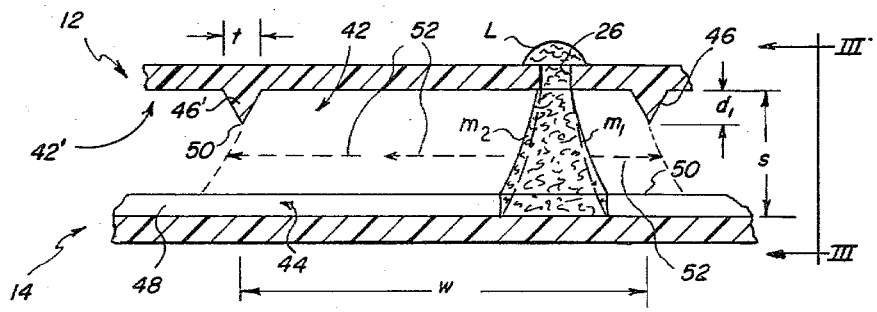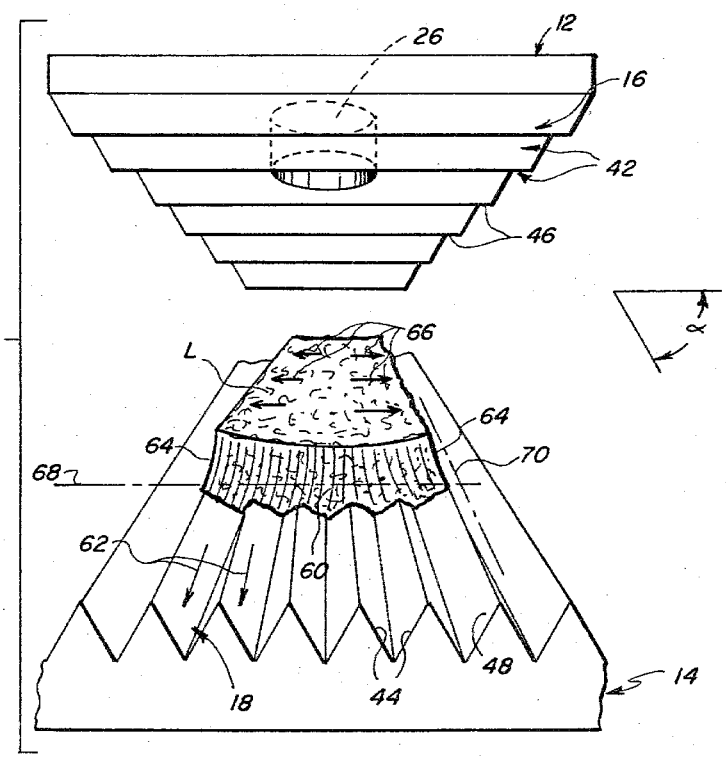

LIQUID TRANSPORT DEVICE AND METHOD

INTRODUCTION (1) Field of the Invention

This invention is directed to a device and method for transporting liquid in controlled, predetermined flow patterns, and, more specifically, to such a device and method that transport liquid across a surface with the menisci of the liquid advancing as wave fronts having a controlled peripheral configuration.

(2) Background of the Invention

Various passive liquid transport devices, that is, those free of moving parts, have been designed to deliver liquid over defined surface areas. For example, liquids have long been spread between two generally smooth surfaces by the use of capillary action, to permit the study, usually microscopic, of the liquid's contents. Examples of such devices are disclosed in U.S. Pat. Nos. 3,198,064, issued Aug. 3, 1965 and 3,961,346, issued June 1, 1976.

The non-uniform smoothness of the exposed surfaces in such devices, however, characteristically results in uncontrolled and undirected capillary flow of the liquid across those surfaces. The consequences of such uncontrolled flow include the possibility of forming trapped air pockets and thus the incomplete wetting of certain portions of the surface. Air pockets are particularly undesirable when undertaking automatic, possibly microscopic, examination of the liquid and/or the wetted surfaces. Such examination cannot tolerate the absence of the liquid in the relevant scanning area, as automated equipment is not capable of ignoring such unwetted areas. Air pockets are a common occurrence when wetting or filling zones of tortuous configuration, e.g., those containing corners around which the liquid must flow.

Another consequence of uncontrolled flow is the formation of rapidly extending irregular streams. These streams when contacting other liquids induce considerable mixing of the liquids. Such mixing can be particularly undesirable when two dissimilar liquids are transported in a device to make a potentiometric measurement relating to the presence or concentration of a common ionic species. For example, serum electrolytes can be analyzed in a device containing two ion-selective electrodes in which serum and a control liquid are passively transported across various surfaces to provide an ionic path for making potentiometric measurements. A specific example of such serum transport is shown in the devices of U.S. Pat. No. 4,053,381, issued Oct. 11, 1977. Mixing of serum and the control liquid under these circumstances can contaminate one of the electrodes with the wrong liquid, and in any event causes an unstable junction potential.

SUMMARY OF THE INVENTION

This invention concerns the discovery of a liquid transport device and method of transport that solves the aforementioned problems by providing a predetermined liquid flow pattern at a controlled rate across a desired surface area.

More specifically, there is provided a liquid transport device comprising two opposing surfaces, spaced apart a distance effective to induce capillary flow of such liquid, and means to permit the introduction of the liquid between the surfaces. Each of the surfaces includes, across at least a portion thereof, means for directing the capillary flow of introduced liquid along predetermined paths. The directing means on each surface are relatively oriented so that at least a portion of the paths dictated by one of the surfaces forms a positive angle with respect to the paths dictated by the directly opposing portion of the other surface. Remarkably, capillary flow of liquid introduced between the surfaces occurs multidirectionally across the surfaces with a predetermined peripheral configuration.

Characterized in another manner, the invention provides a method of transporting a liquid with a predetermined peripheral configuration while maintaining capillary action. The method comprises the steps of introducing liquid between two opposing surfaces that are spaced apart a distance effective to induce capillary flow in the liquid and provide therebetween a transport zone, directing a portion of the introduced liquid to flow across one of the surfaces along a predetermined first series of paths, and simultaneously directing another portion of the introduced liquid to flow across the other surface along a predetermined second series of paths at least a portion of which forms a positive angle with respect to the directly opposing portion of the first path series, whereby the liquid flows multidirectionally between the surfaces.

Thus, in accordance with the present invention, there are provided a liquid transport device and method which insure that liquid flows throughout a defined zone in accordance with a predetermined pattern and in a controlled manner.

In a related aspect of the invention, there are provided such a device and method which insure a multidirectional flow of liquid with a controlled peripheral configuration.

Yet another aspect of the invention is to provide a device and method of liquid transport that insure predictable and controlled flow rates in defined areas.

Still another aspect of the invention is that liquid is transported in the manner described by a device that is entirely passive. Such passive devices are desirable because they do not require the use of moving parts such as are found in pumps and the like. Passiveness drastically reduces costs, eliminates a primary source of breakdowns, and enhances miniaturization.

Other features and advantages will become apparent upon reference to the following Description of the Preferred Embodiments when read in light of the attached drawings.

BRIEF DESCRIPTION OF THE DRAWINGS

FIG. 2 is an enlarged, fragmentary sectional view of the device of FIG. 1, the width of the grooves and the spacing between surfaces being exaggerated for clarity;

FIG. 3 is a fragmentary perspective view taken generally along the line III—III of FIG. 2, portions of the liquid in contact with the upper member having been deleted for clarity;

DESCRIPTION OF THE PREFERRED EMBODIMENTS

The liquid transport device of this invention is applicable to the transport, also described as "spreading", of any liquid over a surface area or through transport zones of many sizes and shapes, flat or curved, regardless of end uses, provided that the surfaces and liquid involved are capable of providing capillary transport. The invention provides such liquid transport in a controlled, multidirectional manner, to produce a predetermined peripheral configuration.

Although the preferred embodiments hereinafter described are those in which the opposed members are generally flat, the invention is not so limited. Any two generally parallel surfaces with appropriate directing means can be used, provided the opposed surfaces are spaced apart a distance that will permit capillary flow of liquid introduced between the members. This distance need not be uniform throughout the device, that is, exact parallism need not be maintained, as long as capillary flow is maintained as further described hereafter. Useful parallel surfaces include curved parallel surfaces, e.g., cylindrical or spherical members one of which has a concave surface that is generally concentric with an opposing convex surface of the other member.

Also, although "drops" are the preferred shape for introducing the liquid, the invention is applicable to liquid transport no matter what form the liquid takes when it is introduced.

Examples of liquids advantageously transported by this device include both aqueous and non-aqueous liquids with or without dissolved, dispersed, or emulsified addenda. The device and method have been found particularly useful for transport of blood and blood serum.

Figure 1:
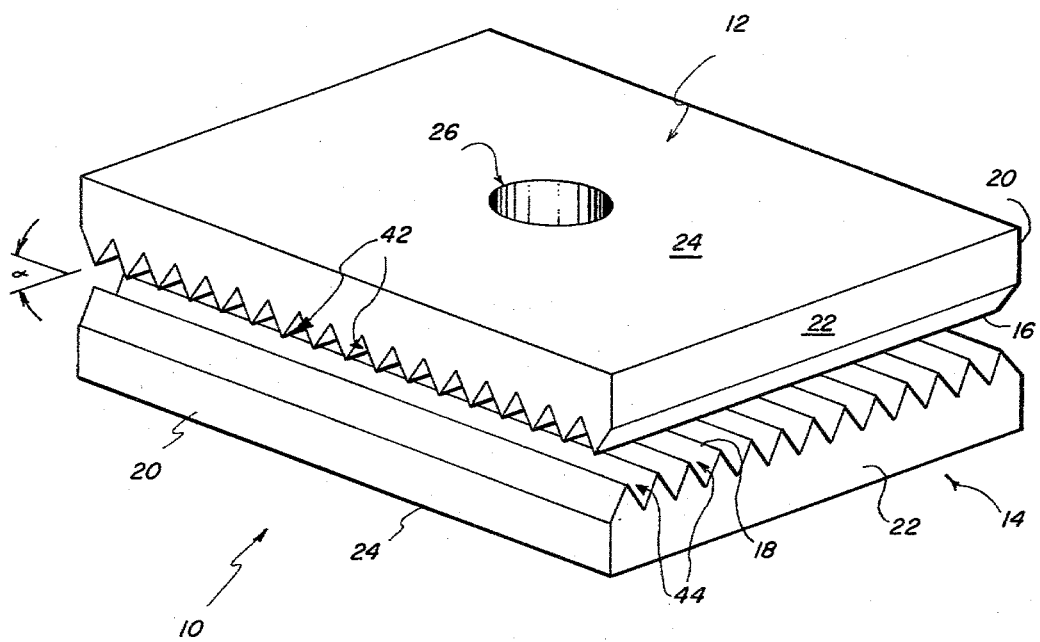
FIG. 1 is an isometric view of a transport device prepared in accordance with the invention, the spacing between parts being exaggerated for clarity.

A liquid transport or spreading device 10 constructed in accordance with the invention to have superior transport properties comprises, FIGS. 1-3, two members 12 and 14 having opposing surfaces 16 and 18, respectively, and additional edge surfaces 20, 22 and back surfaces 24 on the sides of the members opposite to surfaces 16 and 18. Means are provided on surfaces 16 and 18 to control and direct flow of liquid across at least a portion of, and preferably the entire area of, those surfaces. A space of thickness "s" is provided between members 12 and 14. (See FIG. 2). Dimension s is selected to insure that capillary flow of liquid will occur between surfaces 16 and 18, under the influence of directing means 42 and 44. As used herein, "capillary flow" or "capillary transport" is that flow or transport of liquid that occurs between confining surfaces, wettable by that liquid, due to surface tension in the meniscus of the liquid between the surfaces. As is well known, capillary flow is a function of the space "s" between the confining surfaces, and the limit to which such space can be extended depends upon the properties of a given liquid. The space s between the members and the area of surfaces 16 and 18 define the volume of the transport zone.

The two members 12 and 14 can be held apart distance s by a number of constructions, such as a spacer member, not shown, interposed at appropriate intervals through portions of the transport zone. Alternatively, surface 16 can be supported spaced away from surface 18 along or adjacent to edges 20 and 22.

As will be evident, at least one of surfaces 16 and 18 is selected from a wettable material that is substantially impervious to the liquid to be transported. A "wettable surface" is one which, for the liquid to be transported, provides a liquid-vapor contact angle which is less than 90°. Such a contact angle insures the liquid will wet the surfaces to some extent, and is in contrast to the angle that exists when using the same surface material with a liquid such as mercury. As used herein, a "substantially impervious" surface or material is one with respect to which substantially all of the liquid to be transported will move across, rather than penetrate through or into to any appreciable extent. A highly useful embodiment is one wherein both surfaces 16 and 18 comprise a material that is substantially impervious to the transported liquid. As will also be apparent, any listing of such materials depends upon the nature of the particular liquid to be transported, and selection of the appropriate material will be readily evident in light of such liquid.

To permit liquid to be introduced into the transport zone, a liquid access aperture 26 is provided in member 12, extending from surface 24 to surface 16 and disposed above surface 18. The size and shape of the aperture preferably are such as will direct liquid into contact with the surfaces bounding the transport zone. This is, both the surfaces 16 and 18 must be wetted by the continuous volume of the drop, and aperture 26 has a configuration that is not too small to permit this. The transverse dimension of the aperture can also be so large as to prevent contact between the upper surface and a centered drop, but if the drop volume is increased, this deficiency can be overcome. A suitably sized drop therefore should have a volume which at least equals the sum of the volume of aperture 26 and the volume of the transport zone that is to be filled by the liquid. Convenient drop volumes are those between about 5 and about 1000 $\mu$l. The choice of course depends upon the end use of the device. For best results in driving the drop of liquid into the center of the aperture 26, and thus into the transport zone, it is preferred that the shape of the aperture be a regular hexagon, not shown, rather than a circle.

Alternatively, the space between members 12 and 14 left exposed at either edge 20 or 22 can serve as the means to permit the liquid to be introduced. As with aperture 26, the spacing between surfaces 16 and 18 preferably causes the liquid to wet both surfaces.

A highly preferred form of the directing means in surfaces 16 and 18 comprises a pattern of exposed grooves 42 and 44, respectively, in each of such surfaces. Herein the term "groove" refers to a channel, depression or the like and thus each of grooves 42 and 44 is, FIG. 2, the space between two adjacent ridges 46 and 48, respectively. The grooves and ridges of one surface are disposed at an angle alpha ($\alpha$) with respect to the grooves and ridges of the other surface, as is described in detail hereinafter. Each ridge has a top portion or edge 50.

FIGS. 2 and 3 illustrate the manner in which device 10 is effective to provide controlled multidirectional flow. A quantity of liquid "L" of a volume sufficient to wet both surfaces 16 and 18 is placed in aperture 26. However, the condition shown in FIG. 2 is unstable and immediately the menisci $m_1$ and $m_2$ of the liquid move to the positions shown in phantom, filling the width of one groove 42. Meanwhile flow also advances along the length of groove 42. It is observed that a multidirectional flow soon develops, providing a peripheral configuration comprising wave fronts that conform to the linearity, or curvilinearity of the grooves or ridges.

The physical explanation for the linearity or curvilinearity of the wave fronts is not necessary to the practice of the invention, and it is not completely understood. However, it is presently believed that, because of edge effects, the grooves act as repeating, energy barriers to the capillary flow of liquid moving transverse to those grooves, arrows 52 of FIG. 2, as opposed to along those grooves. As is well known, the surface discontinuities created at the top portions 50 of the ridges create energy barriers to capillary flow. Each of the barriers is completely overcome before the next one is breached. Thus, in FIG. 2, if only a portion of the meniscus $m_2$ reaches the left-hand ridge 46', the groove 42' beyond that ridge is a barrier to further flow until the rest of the liquid flowing across groove 42 reaches that ridge. More precisely, although the energy levels favor movement of the liquid to the top portion 50 of ridge 46', the edge at 50 created by the adjacent groove 42' is a temporary energy barrier to further flow by the meniscus into groove 42'. Therefore, less energy represents an increased spacing between the opposed surfaces and is thus required to pull any remaining, lagging portion of $m_2$ up to the top of ridge 46' than is required to move the leading portion of the meniscus shown in phantom at ridge 46', beyond that ridge. When the ridge 46' is reached for the full length of the groove 42 that is carrying liquid, there remains no energy gradient favoring the filling of groove 42 only up to ridge 46'. At that point, assuming sufficient liquid remaining in aperture 26, there is in the liquid sufficient energy to overcome the energy barrier represented by groove 42' beyond ridge 46'.

Thus, a portion of meniscus $m_2$ moves or "jumps" to the next left-hand ridge (not shown). When that occurs, the energy levels favor the movement of all of meniscus $m_2$ to that next ridge before movement continues beyond. Or, liquid flow within groove 44 appears to be directed by the energy barriers or levels represented by the grooves or ridges, respectively, to jump repeatedly from ridge 46 to ridge 46 one ridge at a time. As a result a wave front 60 is formed, FIG. 3, having the linearity or curvilinearity of ridges 46. This wave front advances in the direction of arrows 62.

In the meantime, the same phenomenon is occurring with respect to flow along the length of grooves 42 in the direction of arrows 66, FIG. 3. That is, ridges 48 of the opposite surface create similar energy barriers and flow along the length of grooves 42 will "hesitate" at a ridge 48 rather than cross the energy barrier represented by groove 44 beyond. Only when a wave front has completely reached a given ridge 48 is there no energy gradient favoring movement only up to that ridge. Thus, wave fronts 64 are formed such that, when a portion of the front moves to the next adjacent ridge 48, the energy levels favor the movement of the trailing or remaining portion of the wave front to that same adjacent ridge before the advance portion of the front 64 can move on. As a result, wave fronts 64 take on the linearity or curvilinearity of ridges 48.

The ridge-jumping process continues until the source of liquid L in aperture 26 ceases to have sufficient volume to continue feeding the advancing wave fronts, or the capillary spacing between surfaces 16 and 18 terminates at a boundary of the transport zone such as at edge surfaces 20 or 22, whereby further capillary flow is prevented. If capillary flow ceases because of an open boundary such as at edges 20 or 22, such a boundary can be described as a flow-terminating energy barrier.

Because of the flow control provided by the surface means, e.g., the grooves and ridges, the wave fronts do not accidentally meet each other as in conventional designs so as to confine and trap an air pocket in the transport zone. Instead, the entire area of surfaces 16 and 18 is wetted, and the entire transport zone, defined by such surface areas and the space between them, is filled. Of course, should it be desired, controlled flow to form an air pocket could be achieved.

Figure 4:
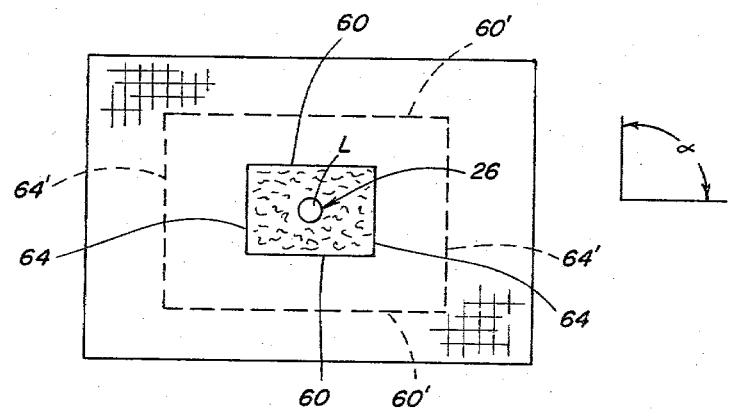
FIGS. 4–6 are plan views of devices like that shown in FIG. 1, illustrating several alternate embodiments thereof and particularly alternate liquid transport patterns.

The preceding discussion of the linearity or curvilinearity of the liquid wave fronts is based upon the flow as viewed overall, in plan. As shown in FIG. 4, when a drop of liquid L is introduced at aperture 26, it encounters surfaces provided with substantially parallel linear grooves. The wave fronts 60 and 64 that form are substantially linear and remain so as the flow proceeds to and beyond the positions 60' and 64', respectively, indicated in phantom.

Thus, the multidirectional flow achieved by the device as described is the overall flow occurring in two or more non-aligned directions as primarily distinguished from unidirectional flow. The multidirectional flow can occur generally in a planar manner, if the opposed surfaces are generally flat, or it can occur three dimensionally if the surfaces are curved.

It will be understood, however, that the microscopic details of the wave fronts are probably more involved. The view in FIG. 3 is only an estimate of the microscopic shape of such wave fronts, especially as seen elevationally. It is believed the wave fronts actually have a curvature about an axis, and specifically that wave front 60 has an axis of curvature 68 and wave fronts 64 an axis of curvature 70. However, whatever the actual microscopic curvature of the wave fronts, e.g., as might appear in a perspective view such as FIG. 3, such is not critical and does not affect the observed overall linearity or curvilinearity of the wave fronts when viewed in plan. In any case, the overall flow of the wave fronts is multidirectionally controlled with a predetermined peripheral configuration.

The pattern of grooves of each surface is preferably continuous; that is, each groove extends either all the way across surface 16 or 18, from an edge 20 or 22 to the opposite edge, or the groove closes upon itself, as in a closed curve, without a break. However, small breaks in the ridges forming the grooves can be tolerated as they will affect the control of the wave fronts to only a negligible extent.

As will be seen, each of the grooves has a substantially greater length than width, as determined by the adjacent ridges. Each pattern of grooves, e.g., grooves 42, provides at least a first predetermined series of flow paths, that is, in the directions of the grooves' lengths. Such directions are the primary flow directions of the grooves. In FIGS. 1 and 2, grooves 42 are illustrated as having a length extending in substantially parallel straight lines, providing essentially straight flow paths. The pattern of grooves 44 provides at least a second predetermined series of flow paths, extending in the directions along the lengths of grooves 44. Grooves 44, FIGS. 1 and 2, are also illustrated as having a length extending in substantially parallel straight lines. The grooves of the respective surfaces are disposed so that the grooves, and therefore the paths of flow of one surface, form an angle alpha ($\alpha$) with respect to the directly opposed portions of the grooves and therefore the paths of flow, of the other surface, FIGS. 1 and 3. The term "directly opposed" as used in reference to a portion of a path or groove of a surface, means a portion that is disposed directly above or below a point, hereinafter "superposition point", on a respective path or groove of the other surface. The angle existing between the two paths or the two grooves of the two surfaces, at the superposition point, is angle alpha. Preferably, angle alpha is measured in a plane parallel to one of the surfaces at the superposition point.

In accordance with one aspect of the invention, angle alpha is positive, that is, non-zero, for at least a portion of the transport zone, and in the case of the patterns of FIG. 1, for the entire transport zone. It is the presence of this positive angle that insures that liquid introduced at aperture 26 will flow through the transport zone in the controlled, multidirectional manner described above. The actual shape or pattern of such overall flow depends upon the value of alpha, the flow rate within the grooves, as described hereinafter, and the curvilinearity, if any, of the lengthwise extension of the ridges (or grooves). As shown in FIG. 1, alpha can be 90°, and in these instances, with substantially parallel, straight grooves 42 and 44, a substantially rectilinear flow pattern proceeds, FIG. 4. That is, wave fronts 60 and 64 are generally perpendicular to each other to provide a predetermined peripheral configuration controlled to the shape of a rectangle. After a passage of time, the wave fronts 60' and 64' are still generally perpendicular.

Figure 5:
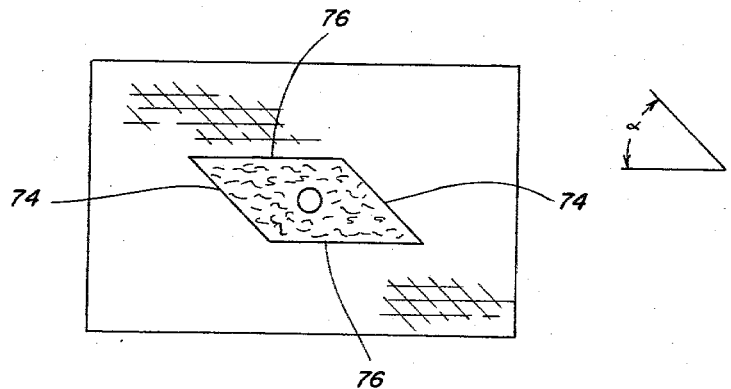

In FIG. 5, angle alpha has a value of 45°. As the grooves in both the members are again substantially straight and parallel, the flow pattern becomes rhomboidal, as delineated by wave fronts 74 and 76.

Figure 6:
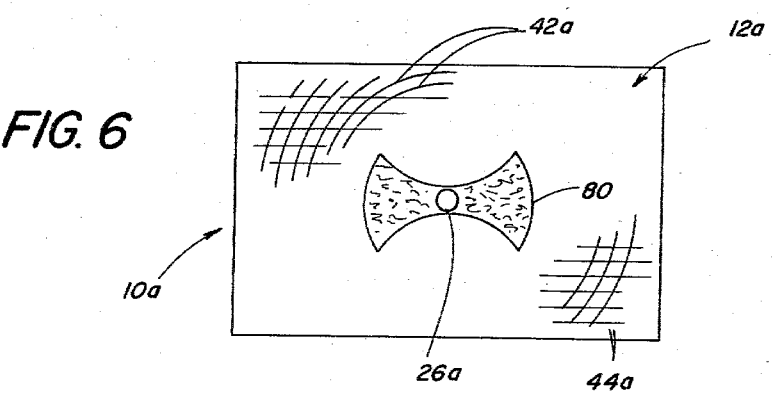

In the embodiment of FIG. 6, curvilinear grooves are utilized. Parts similar to those previously described bear the same reference, to which the distinguishing suffix "a" has been added. Thus, FIG. 6, in device 10a grooves 42a, visible through transparent member 12a, are concentric circles centered upon aperture 26a. Grooves 44a are substantially straight and parallel as before. A flow pattern having an approximately hourglass shape forms as wave front 80 advances, with the long axis extending in the direction of straight grooves 44a. In such a case, angle alpha varies within the pattern from 0° to 90°. Flow of wave front 80 proceeds least rapidly along a line extending from aperture 26a in the direction perpendicular to the direction of the linear grooves, as it is along this line that alpha becomes zero for the infinitesimal portions of the linear grooves that are tangent to the directly opposed circular grooves.

Other curvilinear patterns are also possible, e.g., sine wave patterns, not shown.

It will be appreciated that it is usually of little consequence which of the two members, upper or lower, has which pattern of grooves, so long as at least the portion of the directly opposed grooves over which control of flow is desired form a positive angle as described above.

Certain dimensional variables can provide variations in the performance of device 10. Conveniently, the width "w" of the grooves is defined as the distance from top portion to top portion of adjacent ridges, and the thickness "t" of the ridges is the thickness of the ridges at their base, FIG. 7a. As noted, space s is the distance between surfaces 16 and 18 measured between the bottom surfaces of the grooves. Each ridge of the type shown, whether truncated or peaked, forms an included angle "beta". The depth of grooves 42 is "$d_1$" and of grooves 44 is "$d_2$", and the amount of truncation of the ridges 46, if any, is "$d_3$" (or "$d_4$" for ridges 48.) Finally, each groove or ridge has a radius of curvature "R", R being infinite if the ridges are straight.

The dimensions chosen for s, w, t, beta, R, $d_1$, $d_2$, and $d_3$ can vary, depending upon the liquid being transported, the extent to which it wets surfaces 16 and 18, and the intended use of the liquid so transported. In all cases, capillary flow should be maintained across the surfaces 16 and 18 within the transport zone, and preferably within the grooves 42 and 44, at a rate that is consistent with the intended end use. The selection of particularly desired values of the noted variables to provide a particular capillary flow is a matter of design choice. For uses that contemplate certain lesser flow rates, spacing s can be no greater than $d_1$ and $d_2$, that is, top portions 50 of ridges 46 can contact top portions 50 of ridges 48, FIG. 7b. However, in such instances w should be selected so that multidirectional flow will be achieved notwithstanding a value for s equal to only $d_1$ and $d_2$. If w is reduced below such larger values, when s=($d_1$ and $d_2$), the transport time or time of spreading can become prolonged beyond useful values.

Figure 7A:
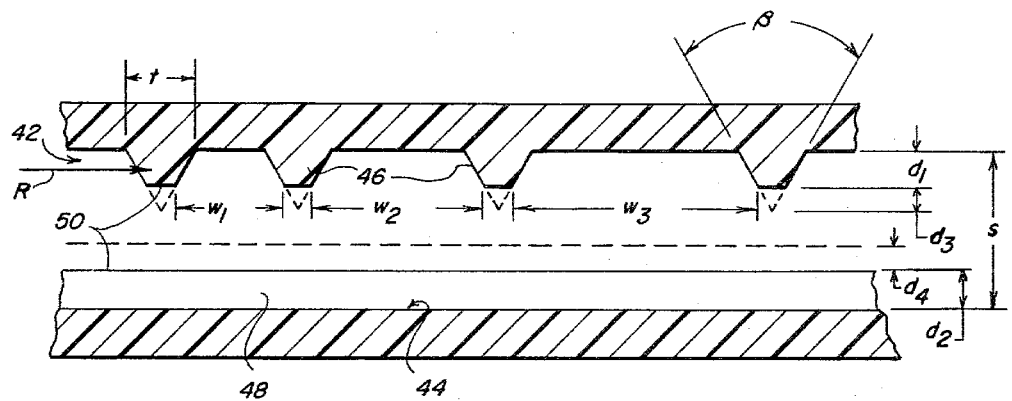
FIGS. 7a and 7b are fragmentary sectional views similar to FIG. 2, illustrating dimensional variables and alternate configurations of the device.
Figure 7B:
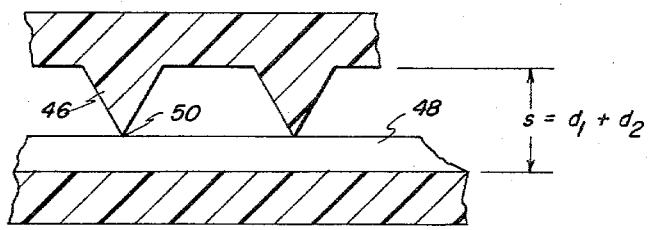

The value of w need not be uniform across an entire pattern, but can be variable, FIG. 7a. For example, $w_n$ can be set equal to n times the width of $w_1$, or each w can be of random widths. However, the width w of grooves 42, for example, does partially control, along with depth $d_1$ or $d_2$, the rate of advance of the wave front within those grooves. The rate has been found to vary roughly as an inverse function of the cross-sectional area of the groove that is transverse to the flow along the length of that groove. That is, the smaller the transverse cross-sectional area of flow through a groove, the faster is the rate of advance of the wave front along that groove, because of capillary action. Furthermore, where the grooves 42 and 44 have uniform, cross-sectional areas different one from the other, the direction of the grooves (measured lengthwise) having the smaller value of that area will be the dominant flow direction.

Figure 8A:
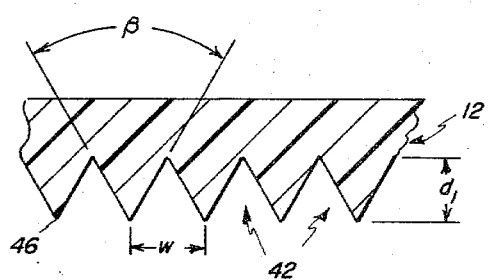
FIGS. 8a and 8b are fragmentary sectional views illustrating the effect of varying angle beta.

Included angle beta in either of the ridges (e.g., 46, FIG. 8a) forming the grooves can become critical if it is too large, or if it is so small as to prevent proper capillary attraction of the liquid being transported, whether or not the ridges are truncated. For most liquids and most materials used in the manufacture of either member 12 or 14, a preferred value for angle beta is about 90°. Values of beta much greater than this tend to cause a loss in control of the advance of the wave front, because the resulting surface approaches a smooth surface that has been noted to lack control. Smaller values of beta can be used, even as small as about 10°, FIG. 8b. When using small values of beta and non-truncated ridges, unless the spacing between the ridges is increased, the liquid might not completely wet the grooves. Although such a design is still useful, the best control over the peripheral configuration of the transported liquid occurs when the grooves are completely wetted. To insure complete wetting, an increase in spacing between ridges can be obtained by the effective elimination of one or more next adjacent ridges (shown in phantom, FIG. 8b), producing flat-bottomed grooves 42. Just how much space is needed is a function of the liquid being transported, specifically its surface tension, as well as of its ability to wet the material forming the surface in question.

Figure 8B:
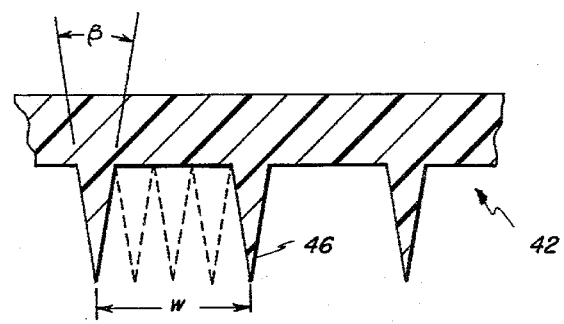

Larger values of beta, e.g., up to about 90°, can also be used in the embodiment shown in FIG. 8b. However, care must be taken that w is not so large that capillary flow is lost or the flow rate becomes too slow.

The preceding analysis assumes that the demarcation between the bottom surface between ridges, and the side wall of the ridges, is a sharp line of intersection, and that top portions 50 form a sharp edge of demarcation with the side walls. However, one can also use curved surfaces for the bottom or top portions, so that there is no clear line of demarcation. In such instances, dimensional variables t, w and angle beta can be approximated only.

The formation of the above-described grooves can be achieved by a number of conventional techniques, including solvent-softening techniques and embossing techniques. For example, a grooved form roller opposed by a pressure roller can be used in the presence of a solvent mist to create a permanent set in the material as it passes through the rollers.

As noted, it is believed that the wave front configuration is determined by energy barriers or levels. It is such energy barriers or levels that confine the flow across each surface 16 and 18 to certain predetermined paths. Other equivalent means can be used, not shown, such as permanent surface treatments of strip portions of generally hydrophobic surfaces 16 and 18 to provide substantially parallel strips that are more hydrophilic than the strips between them. Useful known processes to increase the hydrophilicity of hydrophobic plastic surfaces include exposing alternating strip portions of the surface to elongated corona discharge, e.g., as taught in U.S. Pat. No. 3,376,208, issued on Apr. 2, 1968; flaming those strip portions with a flame at a temperature between about 885° C. and about 2000° C. for a fraction of a second, e.g., as taught in U.S. Pat. No. 3,072,483, issued on Jan. 8, 1963; wetting the strip portions with a weak acid solution of $H_2O_2$ prior to exposing the wetted portions to UV radiation, e.g., as taught by U.S. Pat. No. 3,360,448, issued on Dec. 26, 1967; or the like.

After the liquid is transported or spread through the entire transport zone of device 10, any further processing can be applied to the liquid as desired. The particular nature of such processing is not critical to the invention and can be selected from a variety of techniques. Examples of end uses available include, e.g., clinical analysis of analytes of the liquid, the use of the transported liquid as a photographic developer, and rapid dissolution of certain reagents distributed in the transport zone for reaction with components of the liquid. In those instances in which members 12 and 14 comprise a transparent material, the liquid and its components can be examined under a microscope. In some of such uses, it can be desirable to include a reagent disposed on at least a portion of one or both of the surfaces, such as a buffer, a lysing agent in the case of blood analysis, and/or a compound capable of reacting with the liquid to generate a detectable change in the manner described in U.S. Pat. No. 3,992,158, issued on Nov. 16, 1976.

Yet another use of the device is as a means for providing controlled distribution of the liquid at a uniform rate along the entire edge 20 or 22, FIG. 1. During liquid removal along such edge, the transport device 10 insures that the rate of flow of liquid to that edge is controlled and uniform along that entire edge.

Figure 9:
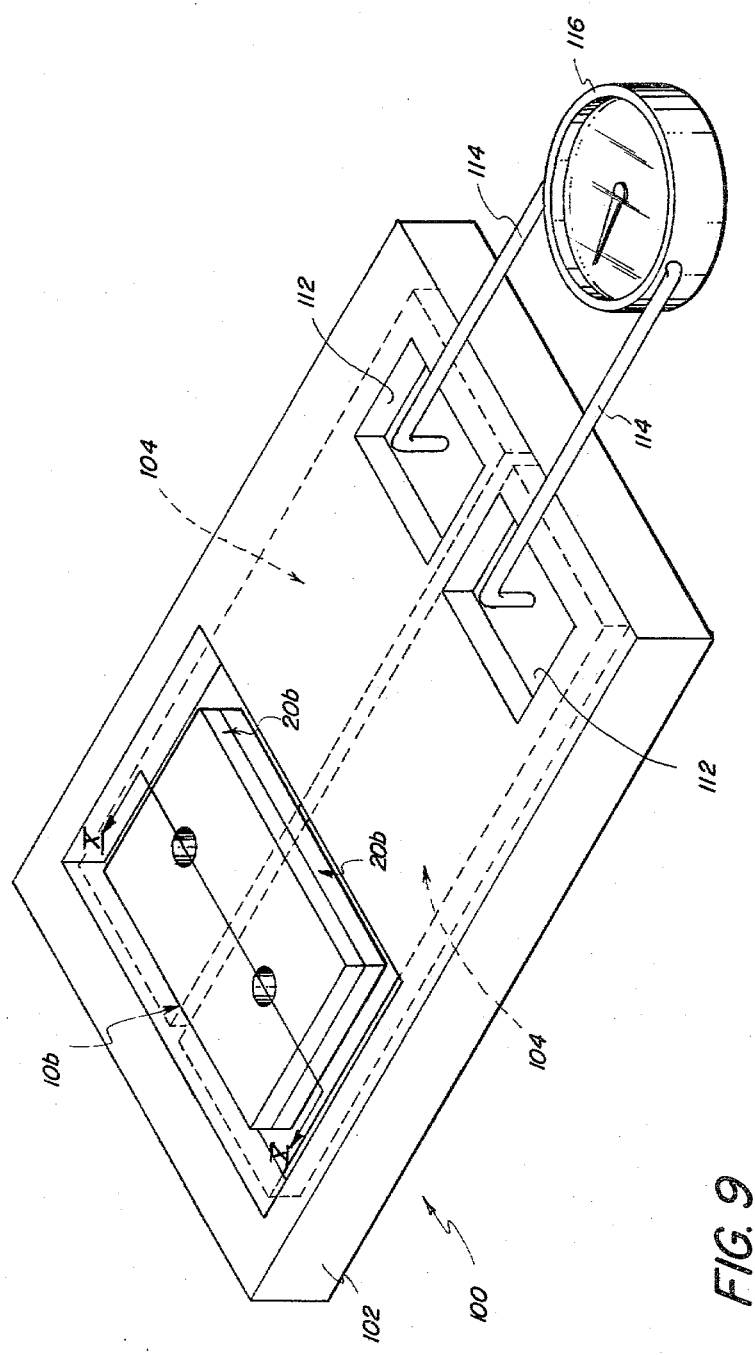
FIG. 9 is an isometric view of an embodiment of the invention, in a device for analyzing ionic activity of electrolytes of a liquid.

A preferred use of the device of the invention features the potentiometric analysis of blood serum after it is spread through the device to a test site where it contacts an adjacent electrode. Parts similar to those previously described bear the same reference numeral to which a distinguishing suffix "b" is added. As described in copending U.S. application Ser. No. 059,816 filed on July 23, 1979 by Richard L. Columbus, entitled Electrode-Containing Device With Capillary Transport Between Electrodes, such a device 10b comprises, FIGS. 9–11, an ion bridge in an apparatus 100 that also includes a frame 102 which mounts a pair of ion-selective electrodes (hereinafter, "ISE") 104, bridged by device 10b. As described in detail in U.S. Pat. No. 4,053,381, issued on Oct. 11, 1977, the details of which are expressly incorporated herein by reference, each ISE 104 is a generally flat multilayered element comprising adjacent layers 106–110, FIG. 10. When a drop of liquid A or B, FIG. 10, such as blood serum, makes contact with layer 106, an ion-selective membrane, the ion $Z \oplus$ of choice which is an analyte of the blood serum is carried or otherwise penetrates to the underlying layers 107–108 where an electrical potential is generated based upon the activity of that particular ion. Layer 107, for example, can be a dried hydrophilic binder containing the salt $Z^{\oplus}X^{\ominus}$. Layer 108 in such instances is the $X^{\ominus}$ salt of an electrically conductive metal $M^{\oplus}$, and metal $M°$ forms layer 109. Because layer 109 is an electrically conductive layer, the potential can be detected by electrometer 116 via probes 114 which penetrate into contact with layer 109 at windows 112. Any difference in these potentials due to two different ion activities of two liquids A and B, one an unknown and one a reference having a known concentration of $Z \oplus$, is registered as a difference potential on the electrometer. This reading then can be converted into a measure of concentration of the ionic analyte $Z \ominus$.

Figure 10:
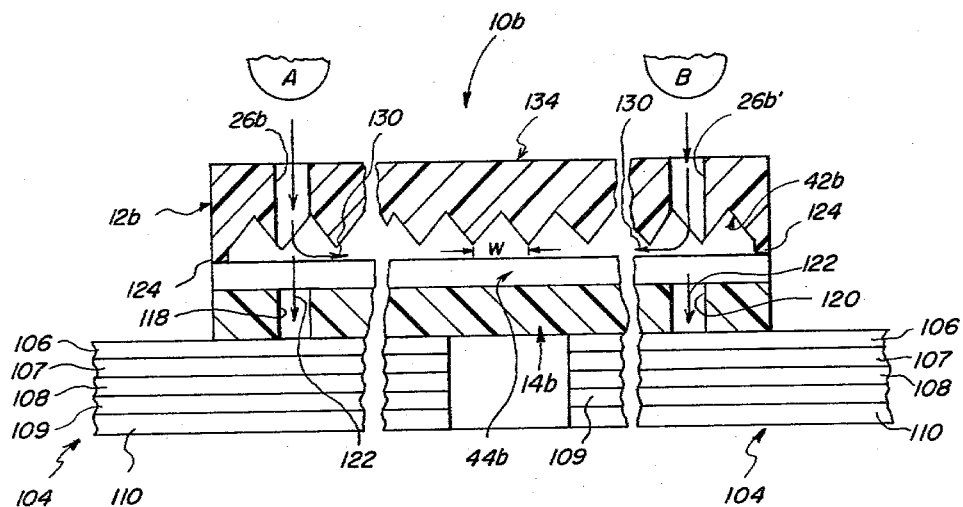
FIG. 10 is a fragmentary sectional view taken generally along the line X—X of FIG. 9.

A pair of holes 26b and 118, and 26b' and 120, are formed above each ISE 104 as liquid access apertures, FIG. 10. It is through these hole pairs that the two drops of liquid A and B move to contact the ISE's, as shown by arrows 122.

Device 10b is used to provide means for ionically connecting the liquid of drop A to the liquid of drop B, FIG. 10, whereby an electrical circuit, including the ISE's and the electrometer, is complete and the potentials generated in the ISE's will register on electrometer 116. In accordance with the invention, this is achieved by the use of members 12b and 14b having opposing surfaces each of which bears a pattern of grooves 42b and 44b, which can be for example sawtooth in shape. Grooves 44b extend from at least the vicinity of aperture 26b to at least the vicinity of aperture 26b', and are preferably substantially parallel and straight. Grooves 42b are superimposed over grooves 44b at an angle alpha of preferably about 90°, and are also substantially parallel and straight. As shown, grooves 42b and their ridges 46b have a width w and thickness t, respectively, of about 13 microns. The same or different dimensions can be used for grooves 44b and their ridges. Grooves 42b, FIG. 10, represent a groove pattern as it would appear magnified approximately 700 times.

Member 12b is spaced from member 14b by edge walls 124, so that grooves 42b are spaced from grooves 44b a distance effective to provide capillary flow of liquid from drops A and B within the space. Walls 124 can be affixed to member 14b by means such as adhesive. Preferably, at least a portion of the space between grooves 42b and 44b is left exposed at edge surfaces 20b of device 10, FIG. 9, whereby air can be vented or expelled as the menisci advance.

Alternatively, the two members can be welded together at appropriate positions, such as by ultrasonic welding, to form bridging studs, not shown, that space the members apart. For example, such welding of the two members at two pairs of relatively small spots, each located so as to bracket apertures 26b and 26b', provides the desired spacing.

Figure 11:
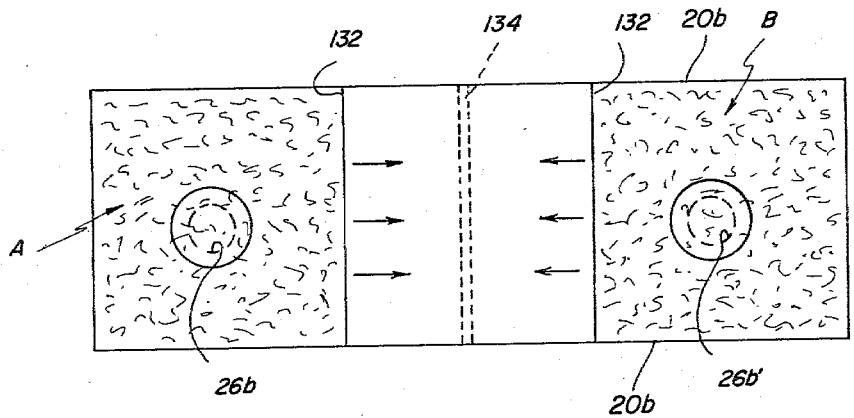
FIG. 11 is a plan view of the ion bridge or FIG. 9, illustrating the advancing liquid wave fronts during use.

Thus, the drops not only penetrate apertures 118 and 120 to contact ISE's 104, they also follow arrows 130 to form two advancing wave fronts 132, FIG. 11. Because grooves 42b and ridges 46b are linear, so are wave fronts 132. Because ridges 46b are parallel throughout device 10b, the wave fronts when they meet form a junction 134 of minimum width between the two different liquids A and B, shown in phantom, FIG. 11. Such minimum width of junction 134 represents a minimum of intermixing, which in turn insures that only source A will contact its electrode. Furthermore, a minimum width of intermixed liquid at 134 is desirable as it provides a stable junction potential and therefore a stable bias rather than a continuously varying bias.

To insure a junction of such minimum width, it is preferred that the flow from apertures 26b and 26b' along grooves 42b fills the width of the bridge from edge 20b to the opposite edge 20b before flow along grooves 44b results in the meeting of the wave fronts 132 at junction 134. One way in which this can be achieved is by providing, as noted above, that the cross-sectional area transverse to flow along groove 42b is smaller than the corresponding area along groove 44b. Alternatively, if junction 134 generally occurs one-half the distance between apertures 26b and 26b', and that distance equals the spacing of the apertures from the edges 20b of the zone, then such cross-sectional areas for grooves 42b and 44b can be about equal.

For use as described, the grooved surfaces of both members 12b and 14b preferably comprise materials that are substantially impervious to blood serum. Examples of such materials include acetates such as cellulose triacetate, cellulose acetate propionate, and cellulose acetate butyrate; polystyrene; polyethylene; polypropylene; ABS plastic; and polycarbonate.

In the transport of blood serum, such as in the above-described use, it is preferred that the groove pattern variables be chosen as follows. For cellulose triacetate grooves having a depth $d_1$ of between about 3 and about 15 microns, $w=t$, and a $w/d_1$ ratio (FIG. 8a) between about 0.35 and about 7.5, the effective spacing s between the two surfaces can be varied between about 0.06 mm and about 0.6 mm for best results. Lesser values of s can be used, except that when the separation distance s approaches $d_1$ plus $d_2$, spreading through the zone becomes extremely delayed. Values of s greater than about 0.6 mm can in some cases destroy the capillary effect and thus the control over the wave front shape and rate of movement.

A preferred range for the width w of the grooves is between about 5 microns and about 5 mm, it being noted that beyond about 5 mm, the rate and direction of spreading becomes so ill-defined as to be insignificantly improved over the control achievable by two smooth surfaces.

Two representative examples of w, t, s, beta, $d_1$ and $d_2$ for the above-described potentiometric analysis of blood serum are as follows:

EXAMPLE 1 w (for surface 12b) = 13.3 microns
w (for surface 14b) = 13.3 microns
t (for surface 12b) = 13.3 microns
t (for surface 14b) = 13.3 microns
s = 63.6 microns
beta = 90°
$d_1$ = 6.8 microns
$d_2$ = 6.8 microns

EXAMPLE 2

As an example of spaced grooves in an otherwise smooth surface, one can have for each of the surfaces:
w = 87.0 microns
t = 1750 microns
s = 250 microns
beta = 60°
$d_1$ and $d_2$ each = 75 microns For either example, to insure that the liquid of each drop does not contact the wrong electrode, a useful spacing of holes 26b and 26b' is about 1 cm when the diameter of the holes is about 3 mm. A useful width of the entire bridge transport zone in such instances, from edges 20b to 20b, is about 6 mm.

Figure 12:
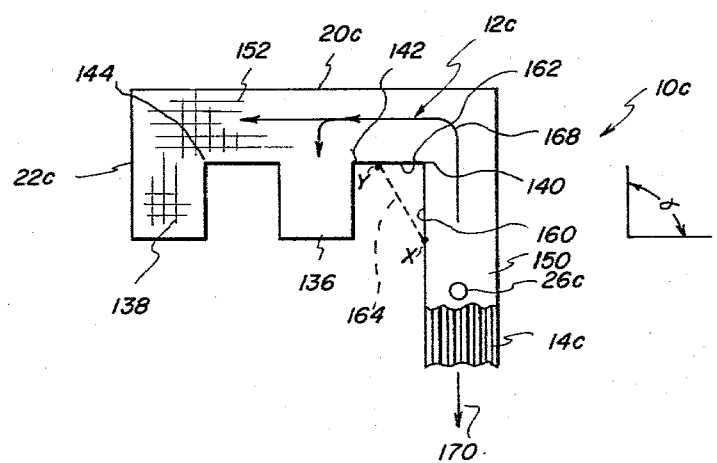
FIG. 12 is a fragmentary plan view of yet another embodiment of the invention.

The embodiment of FIG. 12 demonstrates the ability of a passive device constructed pursuant to the invention to transport liquid around corners within the transport zone. Parts similar to those previously described bear the same reference numeral to which the distinguishing suffix "c" has been added.

Thus, device 10c includes as previously described a lower member 14c and an upper member 12c superimposed over the lower member. The respective opposing surfaces of the two members are both grooved as in the previous embodiment, for example with substantially linear, parallel grooves. The angle alpha between superimposed grooves can be any positive value, e.g., 90° as shown. Aperture 26c permits introduction of liquid, as in previous embodiments.

Unlike the previous embodiments, the boundaries of the transport zone, which can be exposed edges of the transport zone adjacent member edges 20c or 22c or portions of additional closure walls such as wall 124 of FIG. 10, are disposed to provide isolated tests areas 136 and 138, and corners 140, 142 and 144 within the transport zone which must be negotiated in a predictable manner by the transported liquid. Each of these corners represents the point at which a portion of the zone boundaries form an interior angle that is greater than 180°, e.g., an interior angle of 270°.

Thus, the transport zone is divided by corner 140 into two leg portions 150 and 152, portion 150 containing aperture 26c. Portion 152 in turn has extending from it, at corners 142 and 144, respectively, test portions 136 and 138. In order for liquid to pass from aperture 26c into leg portion 152, it must turn corner 40. For the liquid in portion 152 to move into test area 136, it must turn corner 142, and to move into test area 138, it must turn corner 144. Such a transport device can be defined as one in which the transport zone boundaries are so disposed that they permit an imaginary straight line, dashed line 164, FIG. 12, to be drawn between two points X and Y on one or more of the boundaries, such as boundary 160 and boundary 162, respectively, without traversing the transport zone. It is of course the presence of corner 140 which permits such a line 164 to be drawn.

Alternatively, corners 140, 142 and 144 can be curves with no points of discontinuity (not shown), and it is around such curves that the liquid is transported. Such curves provide equivalent interior angles of greater than 180°.

It will be apparent that such a construction permits a plurality of separate tests to be conducted, e.g., in areas 136 and 138, using only a single drop of sample liquid. That drop flows in the direction of arrow 168, first to fill leg portion 150, then to fill leg portion 152 up to corner 142, at which time area 136 fills while the rest of leg portion 152 fills up to corner 144. Test area 138 is then the last area to fill. Each of the transport zone boundaries blocks flow from occurring outside of the zone.

At the same time leg portion 150 is being filled, the drop flows in the opposite direction, arrow 170, to other portions of the zone, not shown, which can be, e.g., a mirror image of portions 150, 152, 136 and 138.

Any desired use can be made of isolated areas 136 and 138. That is, two different analyses of the liquid components can be made at those two portions of the zone.

Without the directing means such as the grooves of members 12c and 14c, and the positive value of angle alpha, it would not be possible to predict that an adequate flow of liquid would reach test areas 136 and 138, and if it did, at what time. Furthermore, flow into the test areas would at best be non-uniform.

The invention has been described in detail with particular reference to certain preferred embodiments thereof, but it will be understood that variations and modifications can be effected within the spirit and scope of the invention.

What is claimed is:

1. A liquid transport device for controlled fluid flow comprising
    two fixedly mounted opposing surface areas substantially all portions of which are spaced apart throughout a zone of intended liquid transport a distance no greater than will maintain a capillary flow of liquid introduced therebetween, and means to permit the introduction of liquid between said surfaces,
    each of said surfaces including, across at least a portion thereof, means for directing capillary flow of introduced liquid along predetermined paths, said directing means on the respective surfaces being relatively oriented so that the paths directed by a substantial portion of one of said surfaces form positive angles with respect to the paths directed by the directly opposing portion of the other surface,
    whereby capillary flow of liquid between said surfaces occurs in a controlled multidirectional manner with a predetermined peripheral configuration.

2. A device as defined in claim 1, wherein at least one of said surfaces is formed of a material that is substantially impervious to the introduced liquid.

3. A device as defined in claim 1, wherein both of said surfaces are formed of material that is substantially impervious to the introduced liquid.

4. A device as defined in claim 1 wherein said directing means of each of said surfaces comprises a pattern of exposed grooves.

5. A device as defined in claim 4, wherein said grooves of at least one of said surfaces are substantially straight and parallel across said surface portion, whereby a substantially linear wave front is formed between said surfaces as the introduced liquid advances across said straight grooves.

6. A device as defined in claim 4, wherein said grooves of both of said surfaces are substantially straight and parallel, and wherein said angles are about 90°, whereby liquid introduced between said surfaces advances as at least two generally perpendicular linear wave fronts.

7. A device as defined in claim 4, wherein said grooves of one of said surfaces are curvilinear and substantially parallel, whereby liquid introduced between said surfaces advances as a curvilinear wave front.

8. A device as defined in claim 4, wherein said grooves are separated by ridges and the top portions of the ridges of one of said surfaces are spaced from the top portions of the ridges of the other surface.

9. A device as defined in claim 4, wherein said grooves are separated by ridges and the top portions of the ridges of one of said surfaces are in contact with the top portions of the ridges of the other surface.

10. A device as defined in claim 4, wherein the the grooves of one of the surfaces have smaller cross-sectional areas, transverse to flow along their length, than the grooves of the other surface to provide preferential flow in the direction of the grooves of said one surface.

11. A passive liquid spreading device for controlled fluid flow comprising
    two opposed generally coplanar surfaces substantially all portions of which are fixedly spaced apart throughout a zone of intended liquid transport a distance no greater than that effective to induce capillary flow of an introduced liquid, and access means to permit the introduction of liquid between said surfaces,
    said surfaces each including, across at least portions thereof, a plurality of exposed grooves formed in a predetermined pattern, at least a substantial portion of said grooves of one of said surfaces being disposed at positive angles with respect to the directly opposed grooves of the other surface to controllably induce the menisci of liquid introduced between said surfaces to advance with a predetermined peripheral configuration.

12. A device as defined in claim 11, wherein said grooves of at least one of said surfaces are substantially straight and parallel across said surface portion, whereby a substantially linear wave front is formed between said surfaces as introduced liquid advances across said straight grooves.

13. A device as defined in claim 11, wherein said grooves of both of said surfaces are substantially straight and parallel, and wherein said angles are about 90°, whereby liquid introduced between said surfaces advances as at least two generally perpendicular linear wave fronts.

14. A device as defined in claim 11, wherein said grooves of one of said surfaces are curvilinear and substantially parallel, whereby liquid introduced between said surfaces produces a curvilinear wave front.

15. A device as defined in claim 11, wherein at least one of said surfaces is formed of a material that is substantially impervious to the introduced liquid.

16. A device as defined in claim 11, wherein said access means comprises an aperture in at least one of said surfaces.

17. A device for controlled distribution of liquid across a zone of intended liquid transport by means of induced capillary forces, said device comprising
   two surfaces respectively having fixedly mounted opposing surface areas substantially all portions of which are spaced throughout a transport zone a distance no greater than that effective to induce capillary flow and to define said transport zone, and access means to permit the introduction of liquid into said zone,
   each of said surface areas having a plurality of grooves constructed in a predetermined pattern, a substantial portion of the grooves of one surface area forming positive angles with respect to the directly opposed grooves of the other surface area,
   whereby liquid introduced into said zone flows with a controlled, predetermined peripheral configuration.

18. A device as defined in claim 17, wherein at least one of said surfaces is formed of a substantially liquid-impervious material.

19. A device as defined in claim 17, wherein said grooves of at least one of said surfaces are substantially straight and parallel through said zone, whereby a substantially linear wave front is formed between said surfaces as introduced liquid advances across said straight grooves.

20. A device as defined in claim 17, wherein said grooves of at least one of said surfaces are curvilinear and substantially parallel throughout said zone, whereby liquid introduced at said aperture produces a curvilinear wave front that advances curvilinearly.

21. A device as defined in claim 17, wherein said access means comprises an aperture located in at least one of said surfaces within said transport zone.

22. A device as defined in claim 17, wherein said surface areas have boundary portions which form an interior angle of greater than 180°.

23. A method of transporting a liquid with a controlled peripheral configuration, comprising the steps of
   introducing liquid between two fixedly mounted opposing surfaces substantially all portions of which are spaced apart throughout a zone of intended liquid transport a distance no greater than that effective to induce capillary flow in the liquid across said zone between said surfaces,
   directing a portion of the introduced liquid to flow across one of said surfaces along a predetermined first pattern of paths,
   and simultaneously directing another portion of the introduced liquid to flow across the other of said surfaces along a predetermined second pattern of paths, the paths of one surface forming positive angles with respect to the directly opposing paths of flow directed by the other surface.

24. A method as defined in claim 23, wherein said zone is defined by boundaries, and further including the step of directing a portion of the liquid to flow around a portion of said boundaries forming an interior angle of greater than 180°.

25. A method as defined in claim 23, wherein said flow across at least one of said surfaces is directed to advance as a linear wave front.

26. A method as defined in claim 23, wherein said flow across at least one of said surfaces is directed to advance as a curvilinear wave front.

27. A method as defined in claim 23, wherein said liquid is a photographic developer solution.

28. In a method of analyzing a liquid, wherein a property of the liquid is detected after it is spread through a defined zone,
   the improved process of spreading said liquid across the area, comprising:
   (a) introducing the liquid between two fixedly mounted opposing surfaces which sandwich the zone, substantially all portions of said surfaces being spaced apart throughout said zone a distance no greater than that effective to induce capillary flow in the liquid,
   (b) directing introduced liquid across one of said surfaces along first predetermined paths, and
   (c) directing introduced liquid across the other of said surfaces along second predetermined paths which form positive angles with respect to said first paths.

29. In a method of analyzing a liquid, wherein a property of the liquid is detected after it is spread through a defined zone of intended liquid transport,
   the process of transporting said liquid across the zone with a controlled peripheral configuration, comprising introducing the liquid between two surfaces having opposed surface areas substantially all portions of which are fixedly spaced throughout said zone a distance no greater than that effective to induce capillary flow and to define said transport zone, each of said surface areas having a plurality of grooves constructed in a predetermined pattern, at least a portion of the grooves of one surface area forming a positive angle with respect to the directly opposed grooves of the other surface area.

30. In a test element for analyzing a liquid at a test site, a liquid transport device for controlling liquid flow to said site, said device comprising
   two fixedly mounted opposing surfaces substantially all portions of which are spaced apart throughout a zone of intended liquid transport a distance no greater than that distance effective to induce capillary flow of introduced liquid, and means to permit the introduction of liquid between said surfaces,
   each of said surfaces including, across at least a portion thereof, means for directing capillary flow of introduced liquid along predetermined paths, said directing means on the respective surfaces being relatively oriented so that the paths directed by a substantial portion of one of said surfaces form positive angles with respect to the paths directed by the directly opposing portion of the other surface,
   whereby capillary flow of liquid between said surfaces occurs in a controlled multidirectional manner with a predetermined peripheral configuration.

31. A test element for the analysis of a liquid comprising
   two fixedly mounted opposing surfaces substantially all portions of which are spaced apart throughout a zone of intended liquid transport a distance no greater than that effective to induce capillary flow of introduced liquid, and means to permit the introduction of liquid between said surfaces, each of said surfaces including, across at least a portion thereof, means for directing capillary flow of introduced liquid along predetermined paths, said directing means on the respective surfaces being relatively oriented so that the paths directed by a substantial portion of one of said surfaces form positive angles with respect to the paths directed by the directly opposing portion of the other surface, whereby capillary flow of liquid between said surfaces occurs in a controlled multidirectional manner with a predetermined peripheral configuration, and a reagent disposed on a portion of at least one of said surfaces for reaction with the liquid.

32. A liquid transport device for controlled fluid flow comprising two fixedly mounted opposing surfaces substantially all portions of which are spaced apart throughout a zone of intended liquid transport a distance no greater than that effective to induce capillary flow of introduced liquid, and means to permit the introduction of liquid between said surfaces, each of said surfaces including, across at least a portion thereof, a plurality of substantially parallel, spaced apart energy barriers to the capillary flow of liquid between said surfaces, at least a substantial portion of the barriers of one of said surfaces being disposed at positive angles with respect to the directly opposed barriers of the other surface to controllably induce the menisci of liquid introduced between said surfaces to advance with a predetermined, peripheral configuration.

33. A device as defined in claim 32, wherein said barriers comprise exposed grooves within said surfaces.

* * * * *

UNITED STATES PATENT AND TRADEMARK OFFICE
CERTIFICATE OF CORRECTION

PATENT NO. : 4,233,029
DATED : November 11, 1980
INVENTOR(S) : Richard L. Columbus It is certified that error appears in the above-identified patent and that said Letters Patent are hereby corrected as shown below:

Col. 5, line 30, delete "is", and insert --represents an increased spacing between the opposed surfaces and is thus--; Col. 5, lines 32-34, delete "represents an increased spacing between the opposed surfaces and is thus", and insert --is--.

Signed and Sealed this

Twenty-sixth Day of May 1981

[SEAL]

Attest:

RENE D. TEGTMEYER

Attesting Officer

Acting Commissioner of Patents and Trademarks